United States Patent
Paskalov et al.

(10) Patent No.: US 7,291,314 B2
(45) Date of Patent: *Nov. 6, 2007

(54) ACTIVATED WATER APPARATUS AND METHODS

(75) Inventors: George Paskalov, Torrance, CA (US); Mark Gorodkin, Los Angeles, CA (US); Viktor Sokolov, Sherman Oaks, CA (US)

(73) Assignee: Hydro Enterprises, Inc., Van Nuys, CA (US)

( * ) Notice: Subject to any disclaimer, the term of this patent is extended or adjusted under 35 U.S.C. 154(b) by 368 days.

This patent is subject to a terminal disclaimer.

(21) Appl. No.: 10/432,208

(22) PCT Filed: Dec. 20, 2001

(86) PCT No.: PCT/US01/49310

§ 371 (c)(1), (2), (4) Date: Sep. 22, 2003

(87) PCT Pub. No.: WO02/058449

PCT Pub. Date: Aug. 1, 2002

(65) Prior Publication Data

US 2004/0069618 A1    Apr. 15, 2004

(51) Int. Cl.
*C02F 1/30* (2006.01)
(52) U.S. Cl. .................... 422/186.29; 422/23; 205/742
(58) Field of Classification Search .................. 422/21, 422/186.04, 186.29; 204/157.15; 205/742
See application file for complete search history.

(56) References Cited

U.S. PATENT DOCUMENTS

| | | | |
|---|---|---|---|
| 4,954,320 A | 9/1990 | Birmingham et al. .. | 422/186.04 |
| 5,326,446 A * | 7/1994 | Binger ........................ | 204/663 |
| 5,387,324 A | 2/1995 | Ibbot et al. .................. | 204/150 |
| 5,624,544 A | 4/1997 | Deguchi et al. ............. | 205/742 |
| 5,655,210 A * | 8/1997 | Gregoire et al. ............ | 422/186 |
| 5,656,171 A | 8/1997 | Strachwitz ................... | 210/695 |
| 5,824,353 A | 10/1998 | Tsunoda et al. .............. | 426/66 |
| 5,866,010 A | 2/1999 | Bogatin et al. ............. | 210/695 |
| 5,876,663 A * | 3/1999 | Laroussi ....................... | 422/23 |
| 5,939,030 A * | 8/1999 | Moxley et al. ......... | 422/186.07 |
| 5,965,009 A | 10/1999 | Shimamune et al. ....... | 205/742 |
| 5,997,590 A | 12/1999 | Johnson et al. ............... | 44/301 |
| 6,033,678 A | 3/2000 | Lorenzo ..................... | 424/401 |
| 6,165,339 A | 12/2000 | Ibbott ......................... | 204/554 |
| 6,193,878 B1* | 2/2001 | Morse et al. .................. | 210/85 |
| 6,974,561 B1* | 12/2005 | Thomason ............. | 422/186.29 |

FOREIGN PATENT DOCUMENTS

JP    11-253522    9/1999

* cited by examiner

*Primary Examiner*—E. Leigh McKane
(74) *Attorney, Agent, or Firm*—Fish & Associates, PC

(57) ABSTRACT

An apparatus subjects water to waves from an RF plasma. This allows continuous production of "activated water" characterized by cluster sizes below about 4 molecules per cluster, water having pH below 4 or above 10, or water having ORP of less than −350 mV or more than +800 mV. The basic frequency of the plasma is preferably between 0.44 MHz and 40.68 MHz, and the plasma is preferably modulated at a frequency between 10 kHz and 34 kHz. Flow rates typically range from 20 l/hr to about 2000 l/hr. Activated water can be used for many purposes, including antimicrobial cleaning of worktable, floor, wall, knife, transport and other surfaces, for example, in meat processing facilities and hospitals.

7 Claims, 1 Drawing Sheet

ACTIVATED WATER APPARATUS AND METHODS

FIELD OF THE INVENTION

The field of the invention is water treatment.

BACKGROUND

Liquid and solid forms of water apparently exist in nature not as independent molecules of $H_2O$, but as clusters of approximately 10-24 molecules of $H_2O$, Obviously monomolecular water can exist transiently in liquids, as intermediates during and immediately following some chemical reactions, and in near vacuums. However, in any substantial quantity of non-gaseous water, the tendency of water to form such clusters is considerable. Current theory provides that the clusters are held together by large numbers of hydrogen bonds that are constantly being formed and destroyed. Water clusters are thought to vary in size depending on numerous factors that affect the hydrogen bonding.

Small cluster (SC) water, defined herein to have a mean size of only 5-6 water molecules per cluster, is reported to have numerous useful characteristics. Among other things, small cluster water is said to provide: improved taste of foods; accelerated absorption of drugs and food through the digestive tract; and prevention of cancer due to reduced production of mutagens in the intestines and reduced activity of enteric microorganisms and digestive tract tissue cells. See U.S. Pat. No. 5,824,353 to Tsunoda et al. (October 1998). Tsunoda et al. and all other publications identified herein are incorporated by reference in their entirety.

Electrical, magnetic, chemical, and acoustical methods have all been utilized in producing small cluster water: Electrical and magnetic methods typically involve running water past closely spaced electrodes. Examples are set forth in U.S. Pat. No. 5,387,324 (Feb. 1995) and U.S. Pat. No. 6,165,339 (Dec. 2000), both to Ibbott. Usually field strength is adjusted by moving the electrodes or magnets with respect to one another. See, e.g., U.S. Pat. No. 5,866,010 to Bogatin et al. (Feb. 1999). In other instances field strength is adjusted by altering the path of the water. See e.g. U.S. Pat. No. 5,656,171 to Strachwitz (Aug. 1997), which describes curved piping through magnetic field. U.S. Pat. No. 6,033,678 (Mar. 2000) and U.S. Pat. No. 5,711,950 (Jan. 1998) both to Lorenzen, describe production of reduced cluster water by passing steam across a magnetic field.

Chemical methods typically involve adding electrolytes and polar compounds. The U.S. Pat. No. 5,824,353 patent to Tsunoda, et al. teaches production of reduced cluster size water using a potassium ion concentration of 100 ppm or more, and containing potassium ions, magnesium ions and calcium ions in a weight ratio of potassium ions:magnesium ions:calcium ions of 1:0.3-4.5:0.5-8.5. Other chemical methods include use of surfactants, and clathrating structures that cause inclusion of one kind of molecules in cavities or lattice of another. See U.S. Pat. No. 5,997,590 to Johnson et al. (issued Dec. 1999).

Acoustical methods typically involve subjection of water to supersonic sound waves. See U.S. Pat. No. 5,997,590 to Johnson et al. (issued Dec. 1999).

A Japanese company currently sells a water purifying system that is said to produce water having cluster size of 5-6 molecules. The system, marketed under the name Microwater™, passes tap water past electrodes. Water passing closer to a positive electrode tends to become acidic. The company's literature reports that the acidic water (termed oxidized or hyperoxidized water) is said to be useful as an oxidizing agent to sterilize cutting boards and treat minor wounds. Other suggested uses are treating athlete's foot, minor burns, insect bites, scratches, bedsores and post-operative wounds. The company's literature also reports that the acidic water has been used agriculturally to kill fungi and other plant diseases. Water passing closer to a negative electrode tends to become alkaline. The alkaline water (termed reduced water) is said to be beneficial when taken internally. Such water is said to inhibit excessive fermentation in the digestive tract by indirectly reducing metabolites such as hydrogen sulfide, ammonia, histamines, indoles, phenols, and scatols.

U.S. Pat. No. 5,624,544 to Deguchi et al. (Apr. 1997) describes such a system. Deguchi et al. claim that oxidizing streams down to pH 4.5 and reducing streams up to pH 9.5 can be achieved on a continuous basis, but that waters having pH 2.5 to 3.2 or pH 11.5 to 12.5 cannot be produced continuously for a long period. It is thought that these limitations are due to the known methods and apparatus being incapable of efficiently reducing the cluster size below about 4 molecules per cluster.

Thus, there is still a need to provide methods and apparatus that can continuously produce substantial quantities of water having cluster sizes below about 4 molecules per cluster, or water having pH below 4 or above 10, or water having ORP of less than −350 mV or more than +800 mV. Water having these characteristics would be much more active than known waters. Thus, there is a continuing need to provide methods and apparatus that can produce such highly active waters.

SUMMARY OF THE INVENTION

The present invention provides methods and apparatus for continuously producing water having cluster sizes below about 4 molecules per cluster, or water having pH below 4 or above 10, or water having ORP of less than −350 mV or more than +800 mV. The terms "continuously producing" and "continuously produced" are used herein to mean that at least 800 ml/min of waters having these characteristics can be produced by a single device for at least one hour without interruption.

A preferred class of apparatus subjects water to waves from an RF plasma. The basic frequency of the plasma is preferably between 0.44 MHz and 40.68 MHz, and the plasma is preferably modulated at a frequency between 10 kHz and 34 kHz. Typically two outlets are used, one delivering acidic water having a measured pH of less than 4, and the other delivering alkaline water having a measured pH of greater than 10. Flow rates typically range from 20 1/hr to about 2000 1/hr, although multiple configurations and sizes of device are also contemplated, so that lower and higher flow rates are possible.

Activated water can be used for many purposes, including antimicrobial cleaning of work table, floor, wall, knife, transport and other surfaces. Especially contemplated uses are in meat processing facilities and hospitals.

Various objects, features, aspects, and advantages of the present invention will become more apparent from the following detailed description of preferred embodiments of the invention, along with the accompanying drawing.

DETAILED DESCRIPTION

Figure 1:
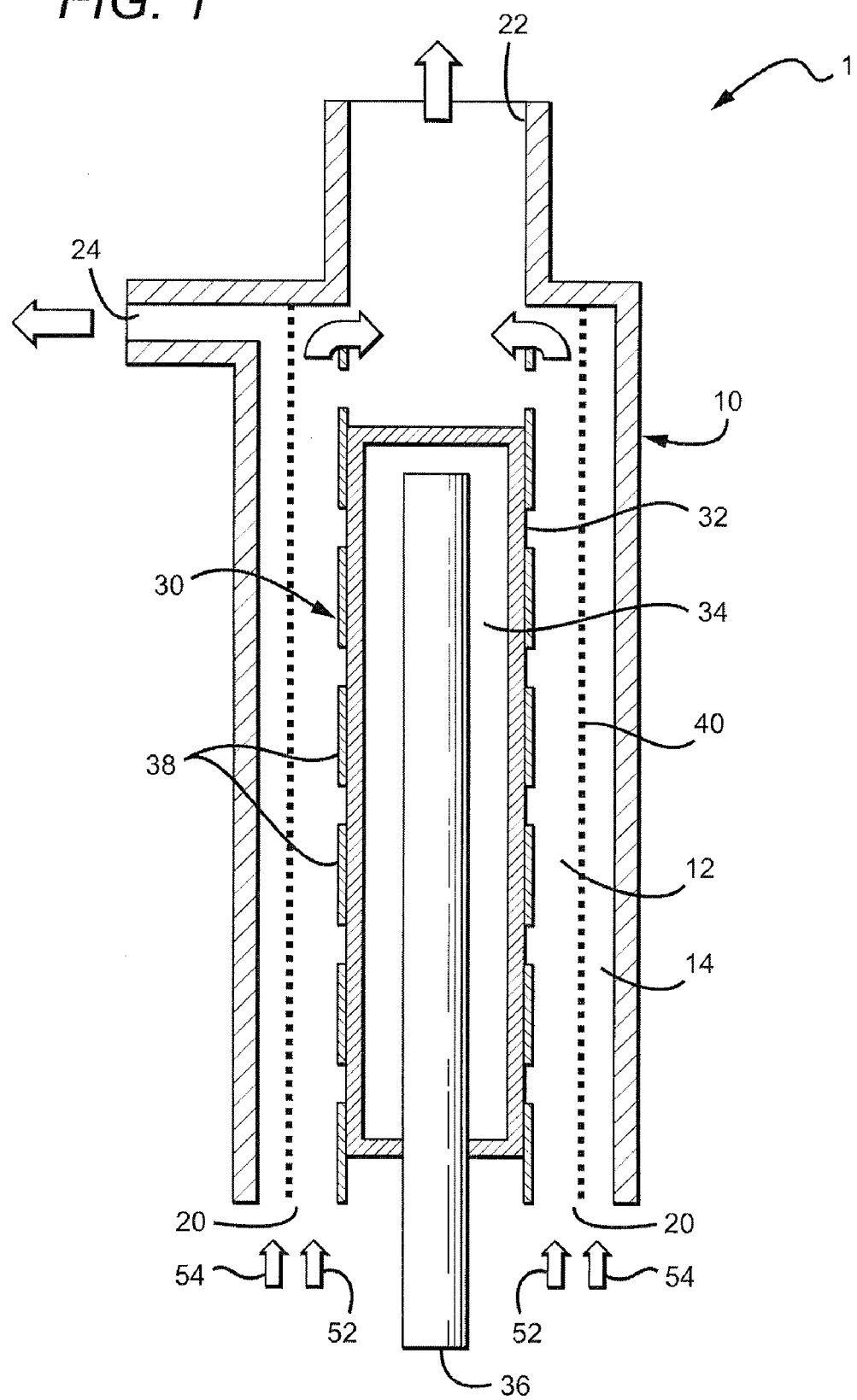
FIG. 1 is a vertical cross section of an activated water generator.

In FIG. 1 an activated water generator 1 generally includes a vessel 10 that has an inlet 20 and two outlets 22, 24, and that encloses a plasma generator 30. Plasmas are conductive assemblies of charged particles, neutrals and fields that exhibit collective effects. Plasma generator 30 is preferably a "cold" type plasma device, which term is used herein to mean a gas of ionized atoms cooler than 10,000° K. A membrane 40 disposed between the vessel 10 and the plasma generator 30 defines an inner space 12 and an outer space 14. With the plasma generator 30 in operation, a first stream 52 of water enters the vessel 10 at inlet 20, flows through inner space 12, and exits the vessel at outlet 22. A second stream 54 also enters the vessel 10 at inlet 20, but flows through outer space 14 and exits the vessel at outlet 24.

Vessel 10 can be any suitable size and shape, as long as water being treated is subjected to energy from the plasma under conditions that produce the desired characteristics in the treated water. Thus, although the vessel 10 in FIG. 1 is substantially cylindrical, with a circular cross-section, other suitable vessels may have a polygonal, oval or other horizontal cross section. Small units are contemplated, for example, where the vessel cavity is only about 200 ml or less. On the other hand large units are contemplated that have an internal volume of at least 10l, as well as everything in between. Unless otherwise stated, ranges are deemed herein to be inclusive of the stated endpoints. Vessel 10 is preferably constructed of stainless steel 316 to reduce corrosion effects, although any sufficiently strong and resistant material could be used, including for example titanium, tantalum, stainless steel coated with titanium, molybdenum, platinum, iridium, and so forth. Multiple water generators can process water in parallel or series.

Water can be subjected to the plasma radiation in any suitable manner. This can be advantageously accomplished by flowing water past the plasma generator 30, but can also be accomplished in a batch mode. For example, a plasma generator can be placed in a container of water, and removed when the water is sufficiently treated. Under those circumstances the system may be used to treat polluted water in situ, i.e. where the water is disposed in soil or some other substance. The pollution may be biological, in which case bacteria, viruses, helminthes, or other microorganisms would be killed or inactivated, or chemical, in which case a chemical could be rendered less harmful through oxidation or reduction, enzymatic destruction, and so forth. Alternatively, water can be treated in a batch mode, ex situ from where it is eventually used.

It is contemplated that the water being processed (i.e. activated) can have substantially any practical purity. Waters preferred that water for processing comprise between about 95% $H_2O$ and 99.99% $H_2O$, but waters having less than 95%, 90%, 85%, 80%, or even 50% are also contemplated. Tap water is thought to typically contain between about 95% $H_2O$ and 99.99% $H_2O$, and is considered to be a good source of water for processing. Distilled water is less suitable because it contains little or no dissolved salts. When processed water has some electro-conductivity it is easier to match plasma and water parameters using the standard matching network system. In this case RF power generator have maximum efficiency and reflected power is minimum.

In this particular example, the plasma generator 30 includes a quartz tube 32 that contains a gas 34, an RF electrode 36, and a plurality of external electrodes 38. The tube 32 can be anywhere from about 60 mm to about 500 mm long or longer. The gas 34 is any suitable plasma gas, including for example argon, argon plus helium, argon plus neon, neon plus helium plus argon, and is held at low pressure, defined herein to mean less than 100 Torr. The gas used in the experimental device of FIG. 1 is Argon, and is filled at a pressure of about 10 Torr. Some experimental data are shown in the Table 1.

| Power | $W/cm^3$ | 7.2 | 32.4 | 61.4 | 62 | 103 | 229 |
|---|---|---|---|---|---|---|---|
| ORP | mV | 780 | 1040 | 984 | 874 | 800 | 790 |
| pH | | 6.4 | 2.3 | 3.3 | 6.4 | 6.3 | 6.3 |

The plasma generator could alternatively be "open", i.e. working pressure up to 1 atmosphere or enclosed at high working pressure, for instance up to 50 Atm.

The electrodes 36, 38 are preferably fabricated from the same type of material as the vessel 10, but are also contemplated to be fabricated from any other suitable material. A first voltage of 500V is applied across the RF electrode 36 and vessel 10, which is electrically grounded for safety and other reason, to generate waves at a basic frequency of between 0.44 MHz and 40.68 MHz, and the resulting waves stimulate the gas 34 to become plasma. A second voltage of 100V is applied across the RF electrode 36 and external electrode 38 to generate waves that modulate the plasma at between 10 kHz and 34 KHz.

Those skilled in the art will recognize that numerous modifications can be made to the preferred embodiment of FIG. 1, while still producing a plasma For example, the quartz tube can be replaced by pyrex, and the external electrodes 38 can be more or less in number than that shown, and can be spaced differently. External electrode 38 should be perforated to allow radiation to escape to the water. Other base and modulation frequencies can be utilized, so long as the resulting plasma is provides energy of sufficient frequency and power to achieve the desired effects on water passing through the vessel 10.

Membrane 40 is permeable to ions, but within that limitation the membrane 40 can be made from many different types of materials. Both high-porous and low-porous materials are contemplated, including ceramic materials based on silica, zirconium oxide, yttrium oxide, and so forth. Some porosity is needed to allow ion exchange to achieve pH gradient. In the experimental version of FIG. 1, the membrane was approximately 300 mm long, which as about 20% longer than the plasma chamber.

The membrane 40 is separated from the plasma generator 30 and the vessel 10 by gaps dimensioned in accordance with the power of the plasma generator 30 and the design flow rate of the system. In the experimental version of FIG. 1, the gap from membrane 40 to plasma generator 30 is 2.5 mm, and the gap from membrane 40 to vessel 10 is approximately 1.5 mm. The flow rate of water through vessel 10 (i.e. through the inlet and exiting either outlet) and is approximately 7 l/min.

The membrane 40 preferably extends substantially the entire length of the external electrodes 38, but can be shorter or longer, and is actually not entirely necessary. The main purpose of the membrane 40 is to separate low pH water from high pH water, so that they exit from different outlets. If that separation is not important a single outlet (not shown) can be used, and the membrane 40 can be eliminated. Benefits can still be achieved, however, because the processed water can still have reduced cluster size, and it is known that activity of water increases as the cluster size is reduced. Very small cluster (VSC) water is defined herein to mean water that has a mean cluster size of less than 4 water molecules per cluster, and is considered to be very active. The term "mean cluster size" is used herein to mean an arithmetic average of cluster sizes in a volume of water. Monomolecular (MM) water is defined herein to mean water that has a mean cluster size of less than 2 molecules per cluster, and is considered to be extremely active. Both VSC and MM waters are much more active that normal water (10-24 molecules per cluster) or even SC water (5-6 molecules per cluster).

Those skilled in the art will recognize that the apparatus of FIG. 1 can be scaled up or down. For example, the apparatus of FIG. 1 can alternatively be viewed as having an overall length of about 100 cm, with the membrane/plasma generator gap being about 7 mm, and the membrane/vessel gap being about 3 mm. Such a device could continuously produce VSC or MM water at a rate of at least 1200 liters/hour. Moreover, even larger devices are contemplated.

It is contemplated that the methods and apparatus described herein can be used to produce very active or extremely active water because the plasma operates at or close to a frequency that breaks apart water clusters. In theory such frequency should vary somewhat depending on the impurities present in the water being treated, and that is precisely what is found. Tap waters from several cities around the United States have been used as sources for experiments, and it is found that a given modulation frequency produces disparate results. The active water generator 1 is therefore preferably "tuned" to improve the breakup of the clusters, and such tuning can advantageously be accomplished by varying the modulation frequency and bias voltage while viewing the output of a ORP meter measuring oxidation reduction potential of one of the processed water streams exiting the vessel 10. Breakup of clusters is considered to optimized by seeking to maximize a positive measured potential or minimize a negative measured potential. In experiments the activity of New York city tap water appears to be optimized at a modulation frequency of approximately 22.7 kHz. The activity of Chicago area tap water appears to be optimized at a modulation frequency of approximately 21.6 kHz. The activity of Los Angeles city tap water appears to be optimized at a modulation frequency of approximately 21.0 kHz. There, when the external electrodes 38 were biased by a negative voltage, the processed water exiting outlet 22 was demonstrated to have pH from 1.8 to 4, ORP from +900 mV to +1150 mV and cluster size was estimated to be from 1 to 3 molecules per cluster. When the external electrodes 38 were biased by a positive voltage, the processed water exiting outlet 22 was demonstrated to have pH from 9 to 11, ORP from −680 mV to +100 mV and cluster size was again estimated to be from 1 to 3 molecules per cluster.

The very activated and extremely activated waters described herein are contemplated to be useful in all manners previously known for activated water. In particular, waters having pH of less than about 3 or more than about 12 are considered useful for antimicrobial effects, and can be advantageously employed on any surface that bacteria, virus, or other microorganisms are considered problematic. For example work table, floor, wall, knife, transport and other surfaces in meat processing plants can be advantageously treated using such waters. Other contemplated surfaces that can advantageously be treated include those in hospitals, doctors offices, or other medical facilities, as well as rest rooms and other areas where blood, feces, or urine may be present. To be effective as an antibacterial agent, it is preferred that at least 50% of the bacteria would be killed or inactivated within 45 seconds of application, although it is more preferable that at least 70%, 80% or even 90% of the bacteria would be killed or inactivated within 1 minute of application. Alkaline waters, especially those having pH or at least 10, are considered useful because of their reducing properties. Thus, such waters may be useful in food processing because they help to retard deterioration of discoloration caused by oxidation. The ability to retard deterioration may be useful in promoting heath in humans and other animals when ingested. Such waters may also be advantageously used in watering plants.

Experimental results establish that at room temperature, water treated in accordance with the teachings herein can remain "activated" for several hours after it is created, but then revert back to normal water within at most a day or two. That reversion process, which may be followed over time as pH deterioration, can be delayed by lowering the temperature of the water. Freezing appears to prevent the "activated" water from reverting back to normal water by at least several weeks. It is also contemplated to prevent reversion of at least the acidic water by adding crystalline clay minerals. See U.S. Pat. No. 5,624,544 to Deguchi et al. (Apr. 1997). Activated water can also be stabilized using a metasilicate salt stabilizer. See U.S. Pat. No. 6,033,678 (Mar. 2000) to Lorenzen. Of course, use of the water as a bacteriocidal agent or in other ways "uses up" the special qualities, and can destroy such qualities almost immediately.

Thus, specific embodiments and applications of very small cluster (VSC) and monomolecular (MM) water have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. An apparatus comprising:
   a wave generator that produces waves at a radio frequency; and
   a processing vessel having a water inlet that subjects a stream of water entering the vessel
      at the water inlet to the waves for sufficient time to directly produce processed
      water with at least one of the following characteristics: a mean cluster size of less
      than 4 molecules per cluster; a measured pH of less than 4, a measured pH of
      greater than 10, a measured Oxidation Reduction Potential (ORP) of less
      than-350 mV, and a measured ORP of greater than +800 mV; and
   including a control portion that directs a first portion of the processed water to exit a first
      outlet of the vessel at the pH of less than 4, and a second portion of the processed
      water to exit a second outlet of the vessel at the measured pH of greater than 10.

2. The apparatus of claim 1 wherein the frequency is between 10 kHz and 34 kHz.

3. The apparatus of claim 1, further comprising a flow path that allows the processed water to pass through the vessel at a rate of at least 20 liter/hr.

4. The apparatus of claim 3 wherein the flow paths that allow the processed water to pass through the vessel at a rate of at least 2000 liter/hr.

5. The apparatus of claim 1 wherein the wave generator comprises a plasma generator.

6. The apparatus of claim 5 wherein the plasma generator produces a cold plasma having a basic frequency of between 0.44 MHz and 40.68 MHz.

7. The apparatus of claim 6 wherein the cold plasma is subjected to a modulation frequency between 10 kHz and 34 kHz.

* * * * *